United States Patent [19]

Koontz et al.

[11] 4,134,019

[45] Jan. 9, 1979

[54] OBJECT SUPPORT SURFACE AND METHOD FOR X-RAY EXAMINATION

[75] Inventors: Paul G. Koontz, Granada Hills; Richard L. Wright, Canoga Park; Arthur M. Cantu, Thousand Oaks, all of Calif.

[73] Assignee: Hipoint Research, Inc., Van Nuys, Calif.

[21] Appl. No.: 818,135

[22] Filed: Jul. 22, 1977

Related U.S. Application Data

[63] Continuation-in-part of Ser. No. 807,050, Jun. 16, 1977.

[51] Int. Cl.² .................. B32B 5/04; G01N 23/04
[52] U.S. Cl. ........................ 250/439 R; 250/473; 428/902
[58] Field of Search ............... 423/447.2; 250/439 R, 250/481, 480, 315, 475, 473; 428/902, 408

[56] References Cited

U.S. PATENT DOCUMENTS

| | | | |
|---|---|---|---|
| 3,778,334 | 12/1973 | Sturgeon | 428/902 |
| 3,897,345 | 7/1975 | Foster | 250/439 R |
| 3,967,126 | 6/1976 | Otto | 250/439 R |

Primary Examiner—Alfred E. Smith
Assistant Examiner—T. N. Grigsby
Attorney, Agent, or Firm—Laney, Dougherty, Hessin & Beavers

[57] ABSTRACT

An improved object support surface for X-ray examinations and a method for carrying out such examinations whereby a source of X-rays is positioned above the surface and an X-ray image receptor is positioned below the surface. The support surface is a highly X-ray transparent and strong material comprised of a fibrous material held in a plastic matrix.

14 Claims, 2 Drawing Figures

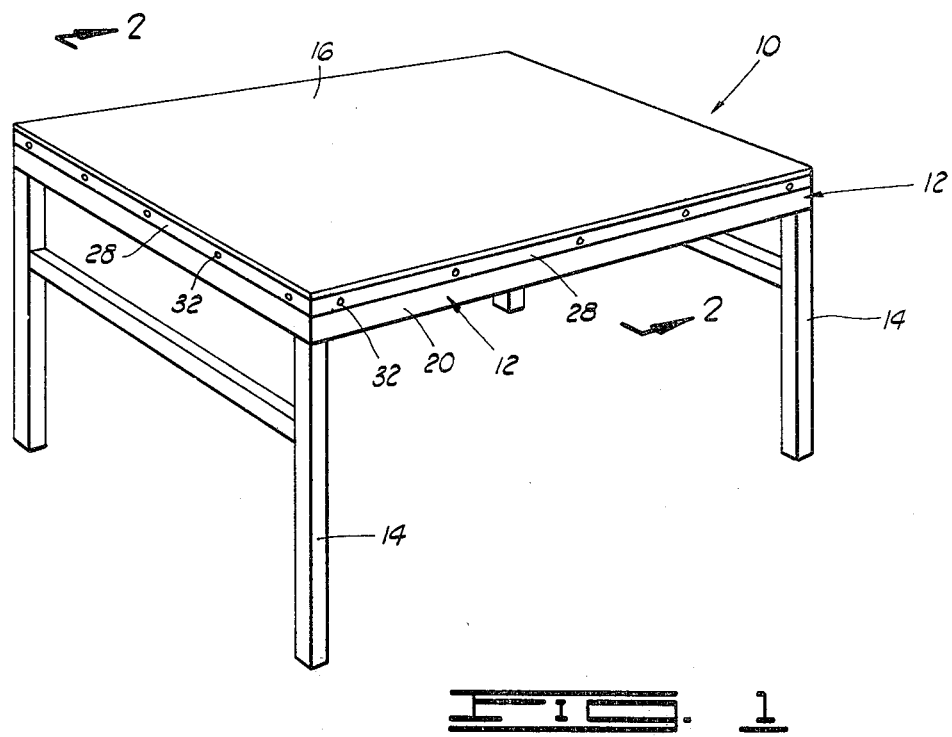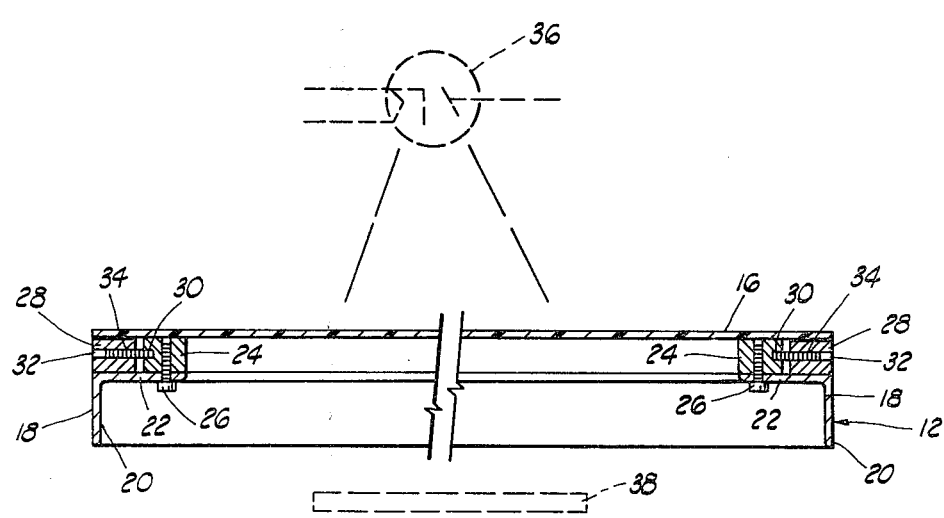

4,134,019

OBJECT SUPPORT SURFACE AND METHOD FOR X-RAY EXAMINATION

RELATED APPLICATION

This application is a continuation-in-part of application Ser. No. 807,050, filed June 16, 1977.

BACKGROUND OF THE INVENTION

1. Field of the Invention

The present invention relates to an improved support surface for supporting an object to be X-ray examined which is highly X-ray transparent and a method for carrying out the examination using the support surface.

2. Description of the Prior Art

X-ray examination tables for supporting an object or patient to be examined have been utilized for many years wherein the source of X-rays is positioned above the table and an X-ray film or X-ray image receptor is positioned below the table. Recently, automated imaging systems have been developed such as CAT (Computerized Axial Tomography) Scanners which utilize patient supporting surfaces through which X-rays are projected. Heretofore, tables and other support surfaces through which X-rays pass before irradiating a film, an X-ray image photoreceptor plate or other X-ray receptor have been formed of relatively X-ray transparent materials such as polycarbonates, cured thermosetting resins of various types and other plastic materials. However, depending upon the particular material used and the thickness thereof, such materials cause X-ray scatter which increases the patient X-ray exposure required for producing a clear X-ray image and reduces the quality of the image.

By the present invention, an improved object support surface for X-ray examinations and a method for carrying out such examinations are provided. The support surface has a high X-ray transparency whereby X-ray scatter and patient X-ray exposure are substantially reduced as compared to heretofore used surfaces.

SUMMARY OF THE INVENTION

A support surface suspended on a frame for supporting an object to be X-ray examined wherein the source of X-rays and the X-ray image receptor are positioned on opposite sides of the support surface. By this invention, the support surface is formed of an extremely thin highly X-ray transparent material having a high tensile strength comprised of a fibrous X-ray transparent material held in a plastic matrix. A method of carrying out an X-ray examination using the support surface is also provided.

It is, therefore, a general object of the present invention to provide an improved object support surface and method for X-ray examination.

Yet a further object of the present invention is the provision of a highly X-ray transparent support surface for supporting an object to be X-ray examined wherein the X-ray source and the X-ray image receptor are positioned on opposite sides of the support surface.

Another object of the present invention is the provision of a highly X-ray transparent support surface for carrying out radiological examinations which is suspended in a frame in a manner such that the tension exerted on the surface can be changed as desired.

Yet another object of the present invention is the provision of an X-ray examination table or the like for supporting a patient to be examined and a method for carrying out the examination whereby the patient X-ray exposure required to produce a high quality X-ray image is substantially reduced as compared to heretofore used methods.

Other and further objects, features and advantages of the present invention will be readily apparent to those skilled in the art upon a reading of the description of preferred embodiments which follows when taken in conjunction with the accompanying drawings.

BRIEF DESCRIPTION OF THE DRAWINGS

FIG. 1 is a perspective view of an X-ray examination table including the object support surface of the present invention.

FIG. 2 is an enlarged sectional view taken along line 2—2 of FIG. 1 which also illustrates the positioning of an X-ray source and X-ray image receptor in dashed lines.

DESCRIPTION OF PREFERRED EMBODIMENTS

Referring now to the drawings, an X-ray examination table including the support surface of the present invention is illustrated and generally designated by the numeral 10. The table 10 is basically comprised of a rectangular frame 12 supported above the floor by a plurality of legs 14 or other base means having a thin highly X-ray transparent support surface or top 16 of high tensile strength suspended thereon. The support surface 16 is a thin composite material preferably comprised of a fibrous material and carbon particles held in a matrix of plastic material such as a thermosetting resin. The frame 12 and base means attached thereto can be formed of a variety of materials, but because of its light weight and high strength aluminum is generally utilized.

As shown best in FIG. 2, the rectangular frame 12 is formed of connected together angle members 18 having downwardly extending legs 20 and horizontally extending legs 22. Connected to the inward portions of the horizontally extending legs 22 are four bars 24 of rectangular shape in cross section. The bars 24 can be attached to the legs 22 of the angles 18 by a plurality of cap screws 26 as shown in FIG. 2, or the bars 24 can be welded or otherwise bonded to the angles 18.

The support surface 16 is bonded at its peripheral sides and ends to four additional bars 28 of rectangular shape in cross section which are positioned exteriorly of the bars 24. The bars 24 include a plurality of outwardly facing recesses 30 disposed therein, and the bars 28 include a plurality of threaded bores 32 positioned in alignment with the recesses 30 in the bars 24. Set screws 34 are threadedly secured in the threaded bores 32 and extend into the recesses 30 in the bars 24. The set screws 34 are threaded inwardly or outwardly to increase or decrease the tension exerted on the support surface 16.

Particularly suitable fibrous materials for forming the support surface 16 are carbon filaments and synthetic organic fibers. Of the organic fibers which can be used, a product of E. I. duPont de Nemours and Company, which is comprised of fibers having an average diameter of about 0.0005 inch, marketed under the trademark "KELVAR" is preferred. Carbon filaments having an average diameter of 0.007 inch are preferred, and both the carbon filaments and organic fibers are formed into tows of about 6000 filaments or mats of woven or randomly oriented filaments.

The tows of fibrous material are impregnated with a curable plastic material, such as by passing the tows through a liquid body of the material, and are laid up in a side-by-side relationship to form a layer or "tape" of desired width. The impregnated tape is then cut into sections which are stacked one on top of the other in a curing fixture in a manner whereby the tows forming adjacent layers are positioned transversely to each other, preferably perpendicularly to each other followed by the curing of the plastic material utilized. When mats of fibrous material are included in the composite material, they are also impregnated with the curable plastic material and are positioned between two or more sections of impregnated tape.

A variety of thermoplastic or thermosetting materials can be utilized including, but not limited to, resins such as polyester, epoxy, phenolic, polypropylene, polystyrene, nylon, polycarbonate, polyurethane and polyphenolene oxides. Thermosetting resins are most suitable for use in forming the support surface of the present invention. Thermosetting phenolic resins are preferred with phenolformaldehyde resins such as bisphenol A-novalak being the most preferred.

The X-ray transparent fibrous materials mentioned above, i.e., carbon filaments and synthetic organic fibers are substantially X-ray transparent, but all of the various thermoplastic and thermosetting materials mentioned above are relatively opaque to X-rays. In order to minimize the quantity of thermoplastic or thermosetting material present in the support surface 16, powdered carbon is preferably mixed with the thermoplastic or thermosetting material utilized in the amount of about 20 percent by volume of the mixture. The stacked sections of tape or mat are preferably impregnated with the mixture of thermoplastic or thermosetting material and powdered carbon in an amount of about 40 percent by weight of the fibrous material and mixture, so that when the stacked sections are squeezed or compressed under pressure, excess amounts of the mixture are removed from the sections and the powdered carbon is distributed throughout the resultant composite material. The powdered carbon fills voids between the tape sections and between the tows forming the sections displacing the thermoplastic or thermosetting material therefrom and providing a carbon-fiber uniformity to the finished composite material, all of which substantially improves the X-ray transparency of the composite material as compared to the materials utilized heretofore. As will be understood, the transversely stacked tows of fibrous material present in the composite material gives the material extremely high tensile strength even when formed in very thin sheets.

The particular number of transversely stacked sections or layers of the impregnated tape utilized to form the surface 16 determines the thickness, flexibility and strength of the surface as well as whether the surface is flat or curved. When an even number of transversely laid-up sections or layers of the tape are utilized, the surface is unbalanced, i.e., the tows of the top and bottom layers are positioned transversely to each other, and upon being removed from the curing fixture, the surface takes on a curved shape, i.e., a shape corresponding to the arc of a circle. When an odd number of layers are utilized, the resulting surface is balanced, i.e., the tows of the top and bottom layers are parallel, and will remain flat when removed from the curing fixture. While an unbalanced curved panel of the composite resin-carbon-fiber material can be used for the support surface 16, a flat balanced panel is preferred. For example, an eleven-layer panel formed of carbon filaments and bisphenol A-novalak resin cured at a temperature of about 300° F while maintaining a pressure thereon of about 1000 psig for a period of 45 minutes has a thickness of about 0.050 inch and is flat.

The support surface 16 can include one or more mats of carbon filaments or organic fibers positioned between equal numbers of transversely stacked tapes of either fibrous material, e.g., four transversely stacked tapes positioned on both sides of the mat. Since organic fibers result in a softer surface which has more resistance to impact damage, it is presently preferred that the top and bottom tapes forming the surface are of organic fibers with the internal tapes being formed of the slightly stronger carbon filaments. However, the surface can be formed entirely of stacked mats of woven fibers, e.g., four mats of woven synthetic organic fibers. The use of mats in forming the surface is economically advantageous since the fibrous materials in mat form are less expensive to produce than in tape form.

As mentioned, the support surface 16 has an extremely high X-ray transparency and a high tensile strength whereby the support surface 16 can be extremely thin as compared to heretofore used materials. For example, the table top 16 can be as thin as 0.050 inch and still have sufficient strength to support a patient or other relatively heavy object thereon. Because of the high X-ray transparency of the support surface 16 and the thinness thereof, when a patient is X-ray examined using the support surface in the manner described hereinbelow, the X-ray dosage to the patient required for producing a high quality X-ray image is substantially reduced as compared to heretofore used X-ray examination support surfaces.

In carrying out an X-ray examination of a patient or other object using the table 10 or other structure having the support surface 16 formed of the highly X-ray transparent material described above suspended thereon, as illustrated in FIG. 2, a source of X-ray 36 and an X-ray image photoreceptor plate or film 38 are positioned on opposite sides of the support surface 16. Generally, the source of X-ray 36 is positioned above the surface 16 with the X-ray image receptor 38 being positioned therebelow, but an opposite arrangement can also be utilized. An object or patient is placed on the support surface 16 and the X-ray source 36 and X-ray image receptor 38 are positioned above and below the portion of the object or patient to be examined. The object or patient is then irradiated with X-rays whereby X-rays pass through the object or patient and through the support surface 16 for a period of time sufficient to form an X-ray image on the receptor 38. The X-ray exposure required to produce a high quality X-ray image on the receptor 38 is substantially less than the exposure heretofore required using prior art X-ray examination tables and support surfaces. Depending upon the particular type of material utilized in the prior art support surfaces, as compared thereto, the method and support surface of the present invention brings about a reduction in X-ray exposure of from about thirty percent to about seventy-five percent.

The tension placed on the support surface 16 and the attitude thereof can be changed as desired by tightening or loosening the set screws 34 which in turn moves the bars 28 to which the surface 16 is attached outwardly or inwardly. Thus, the surface 16 can be tensioned whereby it is flat as illustrated in the drawings or the set screws 34 can be loosened to the point whereby the surface is concave. When concave, the surface 16 is more comfortable to a patient lying thereon and conforms to some degree to the contours of the patient's body.

As will be further understood by those skilled in the art, while the support surface 16 has been described for purposes of this disclosure as an X-ray examination table top, numerous other X-ray examination applications of the support surface formed from the highly X-ray transparent material described are possible.

Thus, the present invention is well adapted to carry out the objects and attain the ends and advantages mentioned as well as those inherent therein. While numerous changes in the formation, construction and arrangement of parts of the invention can be made by those skilled in the art, such changes are encompassed within the spirit of this invention as defined by the scope of the appended claims.

What is claimed is:

1. In a support surface attached to a frame for supporting an object to be X-ray examined whereby a source of X-rays and an X-ray image receptor are positioned on opposite sides of said support surface, the improvement comprising:
    said support surface being suspended on said frame and being formed of a thin highly X-ray transparent material having a high tensile strength comprised of powdered carbon and a fibrous material selected from the group consisting of carbon filaments, synthetic organic fibers and both carbon filaments and synthetic organic fibers, held in a plastic matrix.

2. The apparatus of claim 1 wherein said plastic matrix is a cured thermosetting resin.

3. The apparatus of claim 2 wherein said thermosetting resin is a phenolic resin.

4. The apparatus of claim 3 wherein said fibrous material is synthetic organic fibers and said thermosetting resin is bisphenol A-novalak cured at a temperature of about 300° F and a pressure of about 1000 psig.

5. In a support surface attached to a frame for supporting an object to be X-ray examined whereby a source of X-rays and an X-ray image receptor are positioned on opposite sides of said support surface, the improvement comprising:
    said support surface being suspended on said frame and being formed of a thin highly X-ray transparent material having a high tensile strength comprised of a fibrous material selected from the group consisting of carbon filaments, synthetic organic fibers and both carbon filaments and synthetic organic fibers held in a plastic matrix; and at least one bar bonded to a peripheral portion of said support surface and movably attached to said frame whereby said bar can be selectively moved inwardly to decrease the tension exerted on said surface or outwardly to increase said tension.

6. In an X-ray examination table having a frame and a support surface attached to said frame for supporting an object to be examined whereby a source of X-rays and an X-ray image receptor are positioned on opposite sides of the support surface, the improvement which comprises:
    the support surface being formed of a thin highly X-ray transparent material comprised of powdered carbon and a fibrous material selected from the group consisting of carbon filaments, synthetic organic fibers and both carbon filaments and synthetic organic fibers held in a plastic matrix; and
    means for selectively increasing or decreasing the tension exerted on said support surface attached to said support surface and to said frame.

7. The apparatus of claim 6 wherein said means for increasing or decreasing the tension exerted on said support surface are comprised of one or more bars bonded to peripheral portions of said support surface and movably attached to said frame whereby said bars can be selectively moved inwardly to decrease the tension exerted on said surface or outwardly to increase said tension.

8. The apparatus of claim 6 wherein said plastic matrix is a cured thermosetting resin.

9. The apparatus of claim 8 wherein said thermosetting resin is a phenolic resin.

10. The apparatus of claim 9 wherein said fibrous material is synthetic organic fibers and said thermosetting resin is bisphenol A-novalak cured at a temperature of about 300° F and a pressure of about 1000 psig.

11. A method of X-ray examining an object with a minimum object X-ray exposure comprising the steps of:
    placing said object on a support surface comprised of powdered carbon and a fibrous material selected from the group consisting of carbon filaments, synthetic organic fibers and both carbon filaments and synthetic organic fibers held in a plastic matrix;
    positioning an X-ray source and an X-ray image receptor on opposite sides of said object and said support surface; and
    irradiating said object with X-rays whereby X-rays pass through said object and said support surface for a period of time sufficient to form an X-ray image on said receptor.

12. The method of claim 11 wherein said plastic matrix is a cured thermosetting resin.

13. The method of claim 12 wherein said thermosetting resin is a phenolic resin.

14. The method of claim 13 wherein said fibrous material is synthetic organic fibers and said thermosetting resin is bisphenol A-novalak cured at a temperature of about 300° F and a pressure of about 1000 psig.

* * * * *